United States Patent
Sambandan et al.

(10) Patent No.: US 10,835,631 B2
(45) Date of Patent: Nov. 17, 2020

(54) PHOTOCATALYTIC ELEMENT

(71) Applicant: NITTO DENKO CORPORATION, Ibaraki (JP)

(72) Inventors: Ekambaram Sambandan, Carlsbad, CA (US); Sazzadur Rahman Khan, San Diego, CA (US); Takuya Fukumura, Ibaraki (JP); Hiroyuki Katayama, Ibaraki (JP)

(73) Assignee: Nitto Denko Corporation, Osaka (JP)

( * ) Notice: Subject to any disclaimer, the term of this patent is extended or adjusted under 35 U.S.C. 154(b) by 82 days.

(21) Appl. No.: 15/765,588

(22) PCT Filed: Oct. 6, 2016

(86) PCT No.: PCT/JP2016/004511
§ 371 (c)(1),
(2) Date: Apr. 3, 2018

(87) PCT Pub. No.: WO2017/061124
PCT Pub. Date: Apr. 13, 2017

(65) Prior Publication Data
US 2018/0280559 A1    Oct. 4, 2018

Related U.S. Application Data

(60) Provisional application No. 62/237,962, filed on Oct. 6, 2015.

(51) Int. Cl.
*A61L 9/20* (2006.01)
*B01J 23/10* (2006.01)
(Continued)

(52) U.S. Cl.
CPC ............ *A61L 9/205* (2013.01); *A61L 9/18* (2013.01); *B01J 23/10* (2013.01); *B01J 23/14* (2013.01);
(Continued)

(58) Field of Classification Search
CPC ... A61L 9/205; A61L 9/18; B01J 23/10; B01J 23/30; B01J 23/6527; B01J 23/745;
(Continued)

(56) References Cited

U.S. PATENT DOCUMENTS

2005/0008549 A1 *  1/2005  Hsu .................. A61L 9/205
                                                 422/186
2009/0032390 A1    2/2009  Osterlund
(Continued)

FOREIGN PATENT DOCUMENTS

JP    H10-244130 A    9/1998
JP    2000-300957 A   10/2000
(Continued)

OTHER PUBLICATIONS

Placidus B. Amama et al., "Photocatalytic oxidation of trichloroethylene in humidified atmosphere," 176 Molecular Catalysis A: Chem. 165 (2001).
(Continued)

*Primary Examiner* — Xiuyu Tai
(74) *Attorney, Agent, or Firm* — K&L Gates LLP; Louis C. Cullman; Hal Gibson

(57) ABSTRACT

A photocatalytic element including: a photocatalytic layer containing at least one photocatalytic material; and a light emitting source in optical communication with the photocatalytic material, the light emitting source disposed sufficiently proximal to the photocatalytic material to raise the surface temperature of at least some of the photocatalytic material to a temperature between 10° C. and 90° C. is provided.

16 Claims, 7 Drawing Sheets

(51) Int. Cl.

| | | |
|---|---|---|
| *B01J 23/30* | (2006.01) | |
| *B01J 23/652* | (2006.01) | |
| *B01J 23/888* | (2006.01) | |
| *B01J 35/00* | (2006.01) | |
| *B01J 37/02* | (2006.01) | |
| *B01J 23/48* | (2006.01) | |
| *B01J 37/04* | (2006.01) | |
| *B01J 23/70* | (2006.01) | |
| *B01J 23/14* | (2006.01) | |
| *B01J 23/40* | (2006.01) | |
| *A61L 9/18* | (2006.01) | |
| *B01J 23/745* | (2006.01) | |

(52) U.S. Cl.
CPC .............. *B01J 23/30* (2013.01); *B01J 23/40* (2013.01); *B01J 23/48* (2013.01); *B01J 23/6527* (2013.01); *B01J 23/70* (2013.01); *B01J 23/745* (2013.01); *B01J 23/888* (2013.01); *B01J 35/004* (2013.01); *B01J 37/0215* (2013.01); *B01J 37/04* (2013.01)

(58) Field of Classification Search
CPC ........ B01J 23/888; B01J 35/004; B01J 23/14; B01J 23/40; B01J 23/48; B01J 23/70; B01J 37/0215; B01J 37/04; B01J 37/0244; B01J 21/063; B01J 23/54; F24F 3/166; F24F 2003/1667; B82Y 30/00; B01D 53/864; B01D 53/8675; B01D 2255/802; B01D 2255/9202; B01D 2255/20707; B01D 2255/902; B01D 2255/9025; B01D 2255/40; B60H 2003/0675; Y10T 428/265

See application file for complete search history.

(56) References Cited

U.S. PATENT DOCUMENTS

| | | |
|---|---|---|
| 2011/0064638 A1 | 3/2011 | Molins |
| 2013/0180932 A1* | 7/2013 | Fukumura ............... B01J 27/24 |
| | | 210/749 |
| 2016/0158738 A1 | 6/2016 | Ozaki et al. |

FOREIGN PATENT DOCUMENTS

| | | |
|---|---|---|
| JP | 3109940 U | 6/2005 |
| JP | 2005-351536 A | 12/2005 |
| JP | 2009-131751 A | 6/2009 |
| JP | 2011-072961 A | 4/2011 |
| JP | 2011-110546 A | 6/2011 |
| JP | 2001-340441 A | 12/2011 |
| WO | 2011/148683 A1 | 12/2011 |
| WO | 2015/002326 A1 | 1/2015 |

OTHER PUBLICATIONS

Hisahiro Einaga et al., "Photocatalytic decomposition of benzene over TiO2 in humidified airstream," 1 Phys. Chem. Chem. Phys. 4903 (1999).

International Search Report for PCT/JP2016/004511.

* cited by examiner

PHOTOCATALYTIC ELEMENT

RELATED APPLICATIONS

This application is the U.S. national stage of International Application No. PCT/JP2016/004511, filed Oct. 6, 2017, which claims the benefit of U.S. Provisional Application No. 62/237,962, filed Oct. 6, 2015. The entire disclosures of each application are incorporated by reference herein in their entireties.

TECHNICAL FIELD

The present invention generally relates to reduction of contaminants in air. More particularly, the present invention pertains to a photocatalytic element for removing microbes and malodorous gases from the humid air using a photocatalytic composition and/or reducing the concentration of ethylene in humid air using a photocatalytic composition.

BACKGROUND ART

Visible-light activated photocatalysts can be deployed for self-cleaning, air and water purification and many other interesting applications usually without any post-deployment non-renewable energy costs. This is because the photocatalysts are able to decompose pollutants (like dyes, volatile organic compounds and $NO_x$) using available ambient light like solar radiation or indoor and outdoor lighting. With the anticipated rapid adoption of UV-free indoor lighting (like LEDs and OLEDs), it is imperative to find ways to deploy visible-light activated photocatalysts in indoor applications for instance in cleaning room air in domestic, public and commercial spaces especially in confined spaces like aircrafts, public buildings, etc. Moreover, additional applications for antibacterial surfaces and self-cleaning materials can have wide applicability in the food service, transportation, health care and hospitality sectors.

SUMMARY OF INVENTION

Generally, photocatalytic coatings exhibit low photocatalytic activity, primarily due to low inherent activity of the base photocatalyst material as well as their incompatibility with the often used binders. Thus, there is a need for photocatalytic coatings and/or layers that exhibit desired photocatalytic levels in humid environments. Thus there is a need for a photocatalytic element that improves activity in humid environments.

In some embodiments, a photocatalytic element is described, the element comprising a photocatalytic layer comprising at least one photocatalytic material, a light emitting source in optical communication with the photocatalytic material, the light emitting source disposed sufficiently proximal to the photocatalytic material to raise the surface temperature of at least some of the photocatalytic material to a temperature between 10° C. and 90° C. In some embodiments, the light emitting source may be sufficiently proximal to the photocatalytic element to provide at least 50% reduction in volatile organic compounds in an environment of above 45% relative humidity.

In some embodiments, the light emitting source may be sufficiently proximal to substantially cover at least 85% of the photocatalytic surface area. In some embodiments, the light emitting source may be sufficiently proximal to raise the surface temperature of the photocatalytic material to at least 40° C. In some embodiments, the light emitting source may be a light emitting diode (LED). In some embodiments, the light emitting source may deliver at least 10 $mW/cm^2$ energy at the photocatalytic surface. In some embodiments, the light emitting source may provide light irradiation upon at least 5% surface area of the photocatalytic material. In some embodiments, the light emitting source provides light irradiation at least at one side of the photocatalytic layer. In some embodiments, the optical configuration provides light irradiation at multiple sides of the photocatalytic layer.

In some embodiments, the the photocatalytic layer further comprises at least one co-catalyst. In some embodiments, the co-catalyst can be $CeO_2$, $SnO_2$, $TiO_2$, alkaline titanate, alkali tantalate, and alkali niobate. In some embodiments, the co-catalyst is selected from at least one semiconducting metal oxides or sulphides. In some embodiments, the valence band energy level of the co-catalyst should be higher than that of the photocatalytic material. In some embodiments, the photocatalytic layer further comprises at least one catalyst promoter. In some embodiments, the catalyst promoter can be doped and/or loaded with at least one metal selected from Cu, Fe, Au, Ag, Pt, Pd, Ir, Ru, and Rh or their oxides and hydroxides. In some embodiments, the catalyst promoter may have a concentration of at least 10 ppm. In some embodiments, the at least one catalyst promoter may have at least two electron oxygen reduction functionality. In some embodiments, the photocatalytic material may be an oxide semiconductor having the energy level of the valence band to be lower than 2.85 eV. In some embodiments, the photocatalytic material may have an optical band gap of at least 2.6 eV. In some embodiments, the photocatalytic material can be $WO_3$.

These and other embodiments are described in greater detail below.

DESCRIPTION OF EMBODIMENTS

Figure 1:
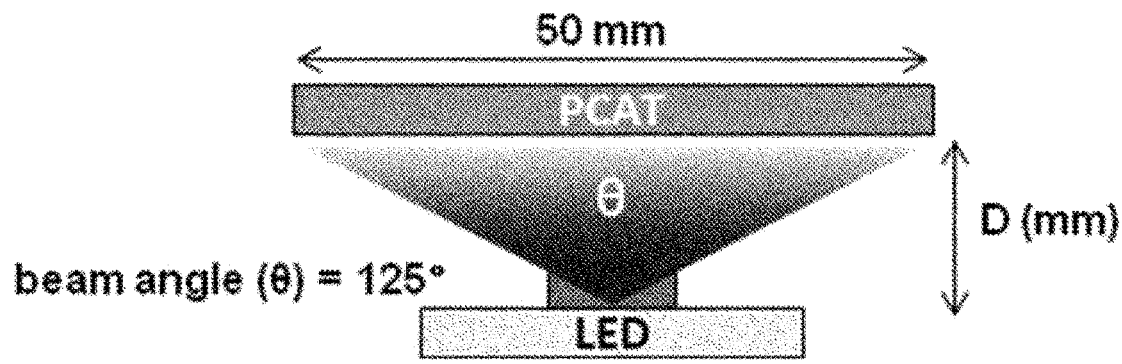
FIG. 1 is a schematic of a photocatalytic element embodiment described herein.

In some embodiments, a photocatalytic element is described, the element comprising a photocatalytic layer comprising at least one photocatalytic material, a light emitting source in optical communication with the photocatalytic material, the light emitting source disposed sufficiently proximal to the photocatalytic material to raise the surface temperature of at least some of the photocatalytic material to a temperature between 10° C. and 90° C. In some embodiments, the light emitting source may be sufficiently proximal to substantially cover at least 75% of the photocatalytic surface area. In some embodiments, the light emitting source may be sufficiently proximal to raise the surface temperature of the photocatalytic material to at least 40° C. In some embodiments, the light emitting source may be a light emitting diode (LED). In some embodiments, the light emitting source may deliver at least 10 mW/cm$^2$ energy at the photocatalytic surface. In some embodiments, the light emitting source may provide light irradiation upon at least 5% surface area of the photocatalytic material. In some embodiments, the light emitting source provides light irradiation at least at one side of the photocatalytic layer. In some embodiments, the optical configuration provides light irradiation at multiple sides of the photocatalytic layer.

A photocatalytic material (or may be referred to as "photocatalyst") includes any material that can activate a chemical reaction as a result of exposure to electromagnetic radiation and/or light, such as ultraviolet or visible light. Photocatalytic material can typically be semiconductor materials which can absorb electromagnetic energy (usually in the wavelength range typically considered as "light") and change the rate of chemical reactions while the photocatalyst remains chemically unchanged. In some embodiments, photocatalyst may be an inorganic solid, such as a solid inorganic semiconductor, that absorbs ultraviolet or visible light. While not wanting to be limited by theory, it is believed that this occurs due to reactive species (able to perform reduction and oxidation) being formed on the surface of the photocatalyst from the electron-hole pairs generated in the bulk of the photocatalyst by said absorption of electromagnetic radiation. In some embodiments, the photocatalyst has a conduction band with energy of about 1 eV to about 0 eV, about 0 eV to about −1 eV, or about −1 eV to about −2 eV, as compared to the normal hydrogen electrode. Some photocatalyst may have a valence band with an energy of about 3 eV to about 3.5 eV, about 2.5 eV to about 3 eV, about 2 eV to about 3.5 eV, or about 3.5 eV to about 5.0 eV as compared to the normal hydrogen electrode. Some photocatalyst may have a valence band with an energy of at least about 2.4 eV, 2.5 eV, 2.6 eV, 2.65 eV, and/or 2.70 eV. Some photocatalyst may have a valence band with an energy of less than about 2.85 eV, 2.80 eV, 2.75 eV, and/or 2.70 eV.

Traditionally, photocatalysts could be activated only by light in the UV regime i.e. wavelength less than 380 nm. This is because of the wide bandgap (>3 eV) of most semiconductors. However, in recent years by appropriately selecting materials or modifying existing photocatalysts, visible light photocatalysts have been synthesized (Asahi et al., Science, 293: 269-271, 2001 and Abe et al., Journal of the American Chemical Society, 130(25): 7780-7781, 2008). A visible light photocatalyst includes a photocatalyst which is activated by visible light, e.g. light that is normally visually detectable by the unaided human eye, such as at least about 380 nm in wavelength. Visible light photocatalysts can also be activated by UV light below 380 nm in wavelength in addition to visible wavelengths. Some visible light photocatalyst may have a band gap that corresponds to light in the visible range, such as a band gap greater than about 1.5 eV, less than about 3.5 eV, about 1.5 eV to about 3.5 eV, about 1.7 eV to about 3.3 eV, or 1.77 eV to 3.27 eV.

Some photocatalysts include oxide semiconductors such as $TiO_2$, $ZnO$, $W_3$, $SnO_2$, etc., and modifications thereof. Contemplated modifications include doping and/or loading. Other materials like complex oxides ($SrTiO_3$, $BiVO_4$) and some sulfides (CdS, ZnS), and some carbides (SiC) and nitrides (GaN) and some oxynitrides (ZnO:GaN) may also display photocatalytic properties. Photocatalysts can be synthesized by those skilled in the art by a variety of methods including solid state reaction, combustion, solvothermal synthesis, flame pyrolysis, plasma synthesis, chemical vapor deposition, physical vapor deposition, ball milling, and high energy grinding.

In some embodiments, the photocatalyst can be an oxide semiconductor. In some embodiments, the photocatalyst can be a titanium (Ti) compound. In some embodiments, the photocatalyst can be a tungsten (W) compound. In some embodiments, the respective Ti or W compounds can be a respective oxide, oxycarbide, oxynitride, oxyhalide, halide, salt, doped or loaded compound. In some embodiments, the respective Ti or W compounds can be selected from or can be $TiO_2$ and/or $WO_3$. In some embodiments, the respective Ti or W compounds can be nanopowders, nanoparticles, and or layers comprising the same. In some embodiments, the photocatalyst may include $WO_3$ and/or $TiO_2$.

Any useful amount of photocatalyst may be used. In some embodiments, the photocatalyst material is present between about 0.01 molar % to about 99.99 molar % of the photocatalytic layer. In some embodiments, the photocatalyst material is present between about 20.00 molar % to about 80.00 molar % of the photocatalytic layer. In some embodiments, the photocatalyst material is present between about 40.00 molar % to about 60.00 molar % of the photocatalytic layer. In some embodiments, the photocatalyst material is present about 50.00 molar % of the photocatalytic layer.

$TiO_2$ and $WO_3$ compounds, e.g., nanopowders, can be prepared by many different methods including thermal plasma (direct current and including radio frequency inductively-coupled plasma (RF-ICP)), solvothermal, solid state reaction, pyrolysis (spray and flame), and combustion. Radio frequency inductively-coupled plasma (e.g. thermal) methods as described in U.S. Pat. No. 8,003,563, which is included herein its entirety by reference, are useful because of low contamination (no electrodes) and high production rates and facile application of precursors either in the gas, liquid or solid form. Hence, radio frequency inductively-coupled plasma processes are preferred. For example, when preparing $WO_3$ nanopowders, a liquid dispersion of additional additives, e.g., ammonium metatungstate, ammonium nitrate and/or glycine, in water (5-20 wt % solid in water) can be sprayed into the plasma volume using a two-fluid atomizer. Preferably, the precursor can be present to about 20 wt % solid in water. The plasma can be operated at about 25 kW plate power with argon, nitrogen and/or oxygen gases. The particles formed from the condensed vapor from the plasma can then be collected on filters. In some embodiments, the particle surface areas range as measured using BET from about 1 m²/g to about 500 m²/g, about 15 m²/g to 30 m²/g, or about 20 m²/g. In some embodiments, the obtained $WO_3$ may be heated from about 200° C. to about 700° C. or about 300° C. to about 500° C.

In some embodiments, a photocatalyst can be doped with at least one naturally occurring element e.g. noble and/or non-noble metal elements. In some embodiments, the non-noble metal elements may be transition metal elements. Doped elements can be provided as precursors added generally during synthesis. Doped elements can be elements that are incorporated into the crystal lattice of the Ti or W compound, for example as substituted within defined positions within the crystal lattice or otherwise interstitially included within the crystal. In some embodiments, the dopant can be selected from one or more elements including alkali metals like Li, Na, K, Cs; alkali earth metals like Mg, Ca, Sr, Ba; transition metals like Fe, Cu, Zn, V, Ti (for W-based compounds), W (for Ti-based compounds), Mo, Zr, Nb, Cr, Co, and Ni; lanthanide and actinide metals; halogens; Group III elements (from the Dmitri Mendeleev/Lothar Meyer style modern periodic table with elements arranged according to increasing atomic number) including B, Al, Ga, In and Tl, Group IV elements including Ca, Si, Ge, Sn; Group V elements like N, P, Bi; and Group VI elements like S and Se. In some embodiments, the photocatalyst can be doped with at least one element selected from C, N, S, F, Sn, Zn, Mn, Al, Se, Nb, Ni, Zr, Ce and Fe. In some embodiments, the photocatalyst may be self-doped, e.g., $Ti^{3+}$ in place of $Ti^{4+}$ in a $TiO_2$ matrix. Details of suitably doped photocatalytic materials are presented in U.S. patent application Ser. 13/741,191, filed 14 Jan. 2013 (United States Patent Publication 2013/0192976, published Aug. 1, 2013, and are hereby incorporated herein their entirety). In some embodiments, the photocatalyst can be loaded with at least one metal. Loaded elements can be provided by post synthesis methodologies like impregnation (Liu, M., Qiu, X., Miyauchi, M., and Hashimoto, K., Cu(II) Oxide Amorphous Nanoclusters Grafted $Ti^{3+}$ Self-Doped $TiO_2$: An Efficient Visible Light Photocatalyst. Chemistry of Materials, published online 2011), photoreduction (Abe et al., Journal of the American Chemical Society, 130(25): 7780-7781, 2008), and sputtering. In some embodiments, the loading may be carried out by electrostatic adsorption (Chee K. Ling, et al, J. App. Sci, 11(8), 1436 (2011)). As a preferred embodiment, loading metals on photocatalysts may be carried out as described in US Patent Publication Number US2008/0241542 which is incorporated here in its entirety by reference. In some embodiments, the loaded element is selected from noble elements. In some embodiments, the loaded element can be selected from at least one noble element, oxide, and/or hydroxide. In some embodiments, the noble elements can be selected from Au, Ag, Pt, Pd, Ir, Ru, Rh or their oxides and/or hydroxides. In some embodiments, the loaded element is selected from transition metals, their oxides and/or hydroxides. In some embodiments, the loaded element is selected from Fe and Cu and Ni or their oxide and hydroxides. In some embodiments, the loaded elements may be chosen from different groups of elements including at least one transition metal and at least one noble metal or their respective oxides and hydroxides.

A co-catalyst includes a material that enhances the photocatalytic properties of a photocatalyst. In some embodiments, a co-catalyst may improve catalytic performance. For example a co-catalyst may increase a rate of catalysis by at least about 1.2, at least about 1.5, at least about 1.8, at least about 2, at least about 3, or at least about 5. One method of quantifying rate of catalysis may include determining a rate of decomposition of an organic compound, such as ethylene. For example, if the concentration of ethylene were photocatalyically decreased to 80% of its original value after 1 hour, or by 20%, an increase in the rate of catalysis of about 2 would result in the amount of ethylene being decreased to 60% of its original value after 1 hour, or by 40%. A rate of catalysis may be measured as a decrease in a compound such as ethylene due to composition, at a given time point, such as about 0.5 hours, 1 hour, 1.5 hours, 2 hours, 2.5 hours, 3 hours, or 5 hours after the photocatalysis is initiated.

Some co-catalyst may be compounds or semiconductors that are capable of being reduced by electron transfer from the conduction band of the photocatalyst. For example, a co-catalyst may have a conduction band having a lower energy than the conduction band of the photocatalyst, or a co-catalyst may have a lowest unoccupied molecular orbital having a lower energy than the conduction band of the photocatalyst. When a term such as "lower energy" and "higher energy" is used to compare a band of a semiconductor or a molecular orbital with band or molecular orbital, it means that an electron loses energy when it is transferred to the band or molecular orbital of lower energy, and an electron gains energy when it is transferred to the band for molecular orbital of higher energy.

Not wanting to be limited by theory, the inventors believe that some co-catalysts may be metal oxides that are capable of reducing $O_2$. For example, $CeO_2$ can reduce $O_2$ gas by electron transfer. In doing so, it is believed that $Ce^{3+}$ transfers an electron to $O_2$ and is converted to $Ce^{4+}$ as a result. In a photocatalyst composition, a photocatalyst may transfer electron to $CeO_2$, thus converting $Ce^{4+}$ to $Ce^{3+}$, and the $Ce^{3+}$ may then reduce $O_2$. $Ce^{3+}$ may also be present as a result of equilibrium processes involving $CeO_2$ and $O_2$, and superoxide radical ion $O_2^-$. $O_2$ and superoxide radical ion in such an equilibrium process may be adsorbed to the surface of solid $CeO_2$ or present in the atmosphere. $Ce^{3+}$ may also be present as a result of oxidation and reduction reactions with cerium species of different oxidation states that may be added intentionally or present as impurities.

Some co-catalysts may be capable of converting atmospheric $O_2$ to superoxide radical ion. For example, $CeO_2$ is capable of converting atmospheric oxygen to superoxide radical ion. It is believed that some of the equilibrium and/or electron transfer processes described above may contribute to this property of $CeO_2$. Such a conversion may occur under a variety of conditions, such as ambient conditions, including for example, normal atmospheric oxygen concentrations, such as about molar concentrations of 10% to about 30%, about 15% to about 25%, or about 20% oxygen; ambient temperature, such as about 0° C. to about 1000° C., about 0° C. to about 100° C., about 10° C. to about 50° C., or about 20° C. to about 30° C.; and pressure, such as about 0.5 to about 2 atm, about 0.8 atm to about 1.2 atm, or about 1 atm. Such a conversion may also occur under elevated or reduced temperature, pressure, or oxygen concentration.

Some co-catalysts may have a valence band or a highest occupied molecular orbital at a higher energy than a valence band of the photocatalyst. This may allow a hole in a valence band of the photocatalyst to be transferred to a highest occupied molecular orbital or a valence band of the co-catalyst. The hole in the valence band or highest occupied molecular orbital of co-catalyst may then oxidize $H_2O$ or $OH^-$ to OH radical. For example, if $WO_3$ is chosen as a photocatalyst, examples of such a co-catalyst may include anatase $TiO_2$, $SrTiO_3$, $KTaO_3$, SiC or $KNbO_3$. In some embodiments, if $WO_3$ is chosen as a photocatalyst, the co-catalyst may include $CeO_2$ and/or $SnO_2$.

In some embodiments, the co-catalyst can be inorganic. In some embodiments, the inorganic co-catalyst can be a binder. In some embodiments, the co-catalyst can be an oxide, such as a metal dioxide, including $CeO_2$, $TiO_2$, or the like. In some embodiments, the co-catalyst can be selected from $SiO_2$, $SnO_2$, $Al_2O_3$, $Fe_2O_3$, $Fe_3O_4$, NiO, and $CeO_2$.

In some embodiments, the co-catalyst can be $Re_rE_tO_s$, wherein in Re is a rare earth element, E is an element or a combination of elements, and O is oxygen, and $1 \leq r \leq 2$, $2 \leq s \leq 3$, and $0 \leq t \leq 3$. In some embodiments, the co-catalyst can be $Re_rO_s$ where Re can be a rare earth metal and r can be greater than or equal to 1 and less than or equal to 2, or can be between 1 and 2 and s can be greater than or equal to 2 and less than or equal to 3 or can be between 2 and 3. Examples of suitable rare earth elements include scandium, yttrium and the lanthanide and actinide series elements. Lanthanide elements include elements with atomic numbers 57 through 71. Actinide elements include elements with atomic numbers 89 through 103. In some embodiments, the co-catalyst can be $Ce_xZr_yO_2$ wherein the y/x ratio=0.001 to 0.999. In some embodiments, the co-catalyst can be cerium. In some embodiments, the co-catalyst can be $CeO_a$ ($a \leq 2$). In some embodiments, the co-catalyst can be cerium oxide ($CeO_2$).

In some embodiments, the co-catalyst can be a non-oxide. In some embodiments, the non-oxide may be a carbide and/or nitride. In some embodiments, the carbide can be silicon carbide.

In some embodiments, the photocatalyst can be $WO_3$ and the co-catalyst can be $CeO_a$ ($a \leq 2$).

In some embodiments, the photocatalytic layer can be formed of the materials described herein.

In some embodiments, a photocatalytic layer can comprise tungsten oxide and a rare earth oxide at a molar ratio of about 0.5 to 2 tungsten oxide: to about 1 rare earth oxide. In some embodiments, the rare earth oxide is cerium oxide ($CeO_2$).

Some embodiments include a photocatalytic layer including tungsten oxide ($WO_3$) and a rare earth oxide at a molar ratio of about 0.5 to 2 tungsten oxide: to about 1 rare earth oxide. In some embodiments, the rare earth oxide is cerium oxide ($CeO_2$).

While not wanting to be limited by theory, the inventors believe that $CeO_2$ may be useful in conjunction with tungsten oxide because of the relative band positions of these materials. Furthermore, it is noteworthy that the index of refraction of $CeO_2$ is substantially the same as tungsten oxide, about 90% to about 110%. In another embodiment, about 95% to about 105%. In some embodiments, the high transparency of the photocatalytic compositions can provide a composition/layer/element of transparency greater than about 50%, 60%, 65% and/or 70%. The low scattering losses due to matched refractive indices contributes directly to a transparent composition.

Some embodiments include a photocatalytic layer wherein the molar ratio of tungsten oxide to cerium oxide is about 0.5 to 2 tungsten oxide: to about 1 cerium oxide. In another embodiment, the molar ratio of tungsten oxide to a rare earth oxide is about 1:1. In another embodiment, the molar ratio of tungsten oxide to cerium oxide is about 1:1. In some embodiments, the photocatalytic composition may include $WO_3$ and $CeO_2$, having a molar ratio ($WO_3$:$CeO_2$) of about 1:5 to about 5:1, about 1:3 to about 3:1, about 1:2 to about 2:1, or about 1:1.

In some embodiments, the photocatalytic layer further comprises at least one co-catalyst. In some embodiments, the co-catalyst can be $CeO_2$, $SnO_2$, (Ce, Sn)$O_2$, $TiO_2$, alkaline titanate, alkali tantalate, or alkali niobate. In some embodiments, the co-catalyst is selected from at least one semiconducting metal oxides or sulphides. In some embodiments, the valence band energy level of co-catalyst should be higher than that of photocatalyst material.

In some embodiments, the photocatalytic layer may further comprise at least one catalyst promoter. In some embodiments, the promoter can be doped and/or loaded with at least one metal selected from Cu, Fe, Au, Ag, Pt, Pd, Ir, Ru, and Rh or their oxides and hydroxides. In some embodiments, the doping may be by combustion methodology. In some embodiments, the promoter may have a promoter concentration of at least 10 ppm. In some embodiments, the at least one promoter may have at least two electron oxygen reduction functionality. In some embodiments, the photocatalytic material may be an oxide semiconductor having the energy level of the valence band to be lower than 2.85 eV. In some embodiments, the photocatalytic material may have an optical band gap of at least 2.6 eV. In some embodiments, the photocatalytic material can be $WO_3$.

In some embodiments, a photocatalytic element comprises a light emitting source in optical communication with the photocatalytic material. As used herein, the term "in optical communication" refers to the condition of an electromagnetic radiation emitting element and the photocatalytic element being configured and/or positioned such that electromagnetic radiation reflected, emitted or transmitted, impinges upon an element comprising photocatalytic material. While not wanting to be limited by theory, it is believed that being too proximal to the photocatalytic material decreased the light illumination area of the photocatalytic material surface to below the necessary or desired threshold. While not wanting to be limited by theory, it is believed that being too distal from the photocatalytic material results in insufficient the light intensity area, heat, etc to below the necessary or desired threshold. In some embodiments, the light emitting source may be disposed sufficiently proximal to the photocatalytic material to raise the surface temperature of at least some of the photocatalytic material to a temperature between 10° C., 20° C., 30° C., 35° C., 40° C., 60° C., 65° C., 70° C., 80° C., 90° C. and or any combination of the aforementioned values, e.g., 10° C. to 90° C., and/or 30° C. to 70° C. In some embodiments, the light emitting source may be sufficiently proximal to raise the surface temperature of the photocatalytic material to at least 30° C., 35° C., and/or 40° C. A schematic of the photocatalytic element in optical communication with the light source is shown in FIG. 1.

In some embodiments, the light emitting source may be sufficiently proximal to the photocatalytic element to provide at least 25%, 35%, 50% and/or 60% reduction in volatile organic compounds (VOC) in a humid environment. In some embodiments, the VOC may be ethylene. In some embodiments, the humid environment may be an environment of above 35%, 40%, 45% relative humidity. In some embodiments, the humid environment may be an environment of between about 35%, 40%, 45% relative humidity to about 60%, 75%, 85%, 90%, 95% and/or any combination of the aforementioned values. In some embodiments, the humid environment may be an environment of about 50% relative humidity. In some embodiments, the humid environment may be an environment of about 85% relative humidity.

In some embodiments, the light emitting source may be sufficiently proximal to the photocatalytic material to provide light irradiation upon at least 5%, 10%, 25%, 50%, 75% surface area of the photocatalyst. In some embodiments, the light emitting source may be sufficiently proximal to substantially cover at least 75% of the photocatalytic surface area. In some embodiments, the light emitting source may deliver at least 50 mW/cm$^2$, 181 mW/cm$^2$, 313 mW/cm$^2$, 565 mW/cm$^2$, energy at the photocatalytic surface.

In some embodiments, the light emitting source may be a visible light source. In some embodiments, the light emitting source may be a blue light source, e.g., 400 nm to about 500 nm emission. In some embodiments, the light emitting source may be 447.5 nm blue light LED with 3V, 300 mA input power. In some embodiments, the LED may have a beam angle of about 125°. Beam angles can be specified by the light emitting diode vendor/manufacturer. In some embodiments, the beam angles may consider the encapsulation materials, thickness and orientation of the light emitting diode with respect to the supporting substrate and/or the radiation receiving surface. In some embodiments, with such a light emitting source, the light emitting source may be within 7 mm to about 15 mm for a 50 mm×50 mm×5 mm photocatalytic material coated ceramic plate. In some embodiments, the minimum distance to cover the entire surface of the photocatalytic element can be described as D=tan[Π−Θ/2]×50 mm/$^2$ with a beam angle (Θ) of about 125° (about 13 mm).

In some embodiments, the light emitting source provides light irradiation at least at one side of the photocatalytic layer. In some embodiments, the optical configuration provides light irradiation at multiple sides of the photocatalytic layer. In some embodiments, the optical configuration provides light irradiation at first side with at least one aforedescribed light emitting diode. In some embodiments, the optical configuration provides light irradiation at first side with an array of aforedescribed light emitting diodes. In some embodiments, the optical configuration that provides light irradiation at multiple sides of the photocatalytic layer can comprise a first light emitting source configured or disposed on a first side of the photocatalytic element and a second light emitting source configured or disposed on a second side of the photocatalytic element. In some embodiments, the second light emitting source can be at least a second light emitting diode and/or a second light emitting diode array. In some embodiments, the second light emitting source configured or disposed on a second side of the photocatalytic element may be a reflector element. In some embodiments, the reflector element can be configured and/or positioned as described on the second side of the photocatalytic element as the first light emitting diode/array is configured and/or positioned on the first side of the photocatalytic element.

EXAMPLES

It has been discovered that embodiments of photocatalytic elements described herein improve the photocatalytic activity in humid environments, e.g., 50% RH and/or 85% RH. These benefits are further shown by the following examples, which are intended to be illustrative of the embodiments of the disclosure, but are not intended to limit the scope or underlying principles in any way.

Example 1

Making Epsilon Phase (W,B)O$_3$

Figure 2:
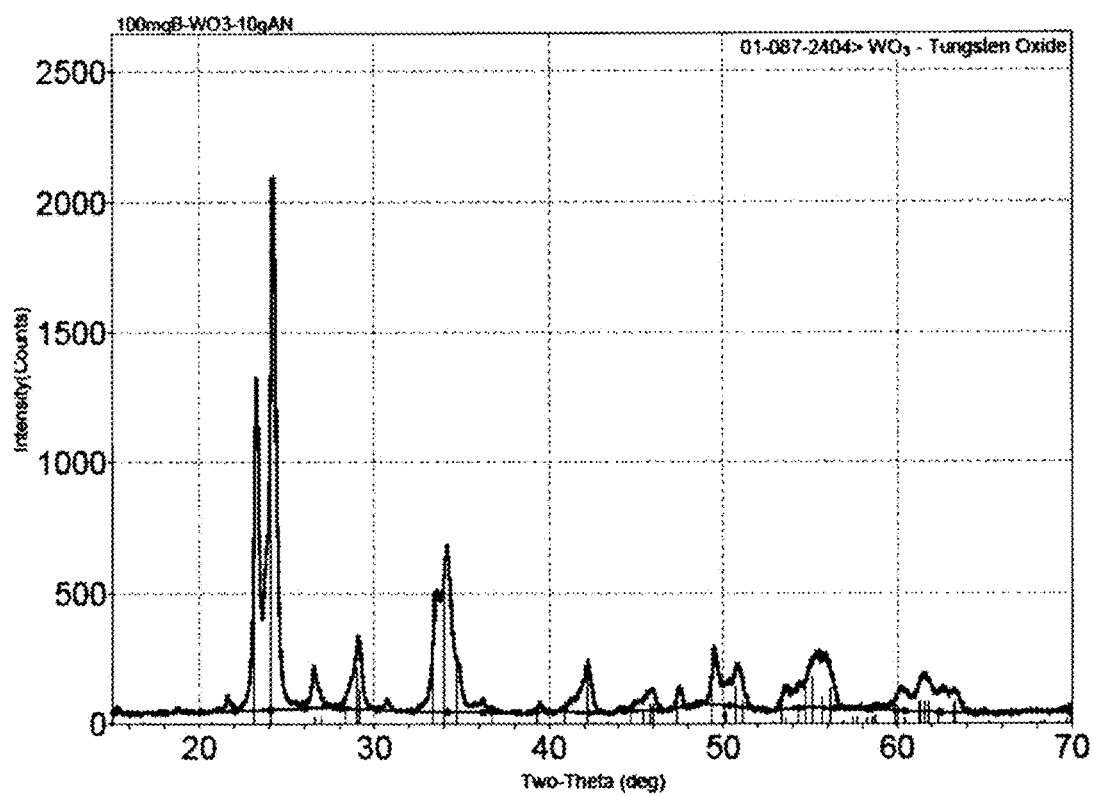
FIG. 2 is a graph showing a result of comparison of powder XRD pattern of boron doped epsilon phase $WO_3$ prepared in Example 1 with a standard epsilon $WO_3$ x-ray diffraction.

Ammonium meta tungstate hydrate (5 g), boric acid (100 mg), carbohydrazide [fuel] (2 g) and ammonium nitrate [oxidizier] (10 g) were dissolved in 35 ml of deionized (DI) water. The aqueous solution was then placed in a muffle furnace, which had been preheated to about 420° C., and then heated for about 15 min or until combustion of the materials was substantially completed. After the combustion of the sample material was completed, the product was annealed in air at about 420° C. for an additional about 15 min. The body color of the powder appeared orange-yellow and boron doped WO$_3$ was confirmed by comparison of powder XRD pattern with a standard epsilon WO$_3$ x-ray diffraction (ICFF PDF card number 01-087-2404) (FIG. 2). Similarly, three more batches of the process were repeated.

Example 2

Making Gamma Phase WO$_3$

Figure 3:
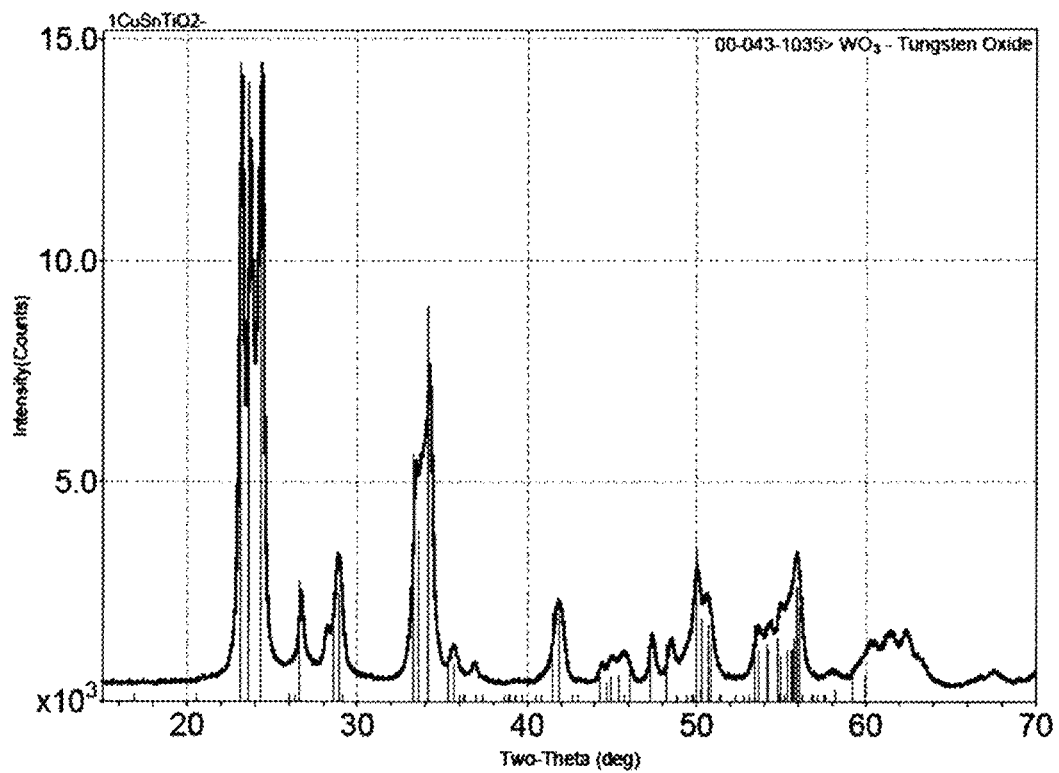
FIG. 3 is a graph showing a result of comparison of powder XRD pattern of gamma $WO_3$ prepared in Example 2 with a standard gamma $WO_3$ x-ray diffraction.

Ammonium meta tungstate hydrate (5 g), carbohydrazide [fuel] (2 g) and ammonium nitrate [oxidizier] (10 g) were dissolved in 30 ml of deionized (DI) water. The aqueous solution was then placed in a muffle furnace, which had been preheated to about 420° C., and then heated for about 15 min or until combustion of the materials was substantially completed. After the combustion of the sample material was completed, the product was annealed in air at about 420° C. for an additional about 15 min. The body color of the powder appeared orange-yellow and gamma WO$_3$ was confirmed by comparison of powder XRD pattern with a standard gamma WO$_3$ x-ray diffraction (ICFF PDF card number 00-043-1035) (FIG. 3). Similarly, three more batches of the process were repeated.

Example 3

Making 0.02 wt. % Ratio Pt Doped Gamma Phase WO$_3$

Figure 4:
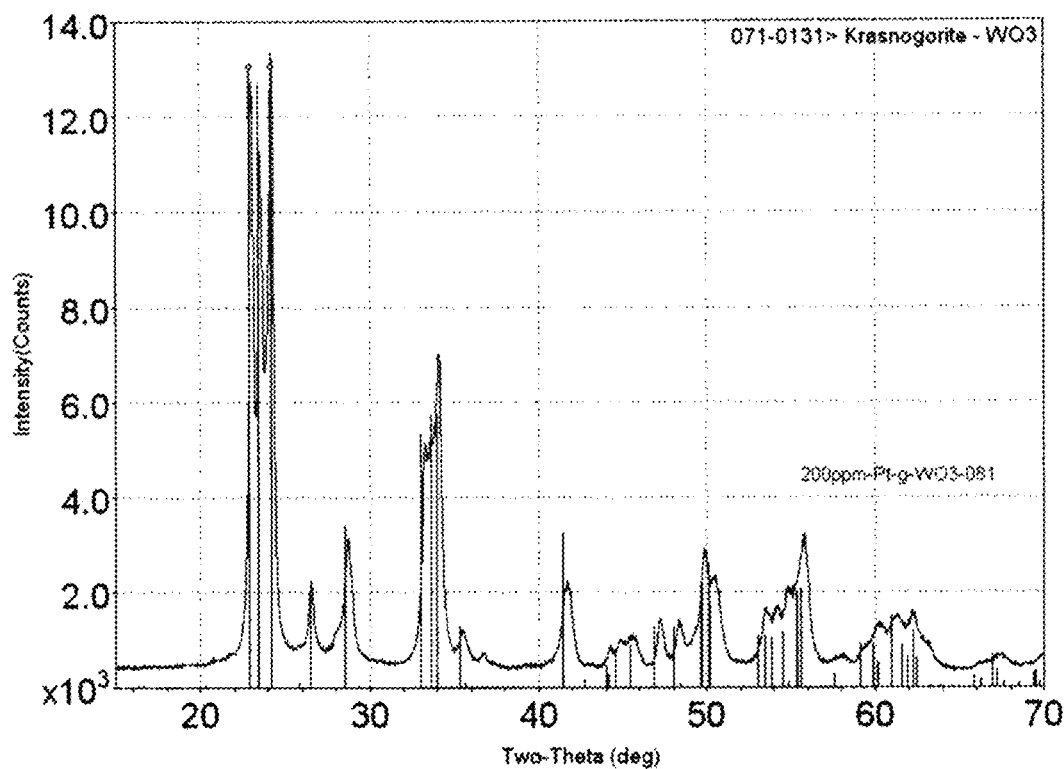
FIG. 4 is a graph showing a result of comparison of powder XRD pattern of Pt doped $WO_3$ prepared in Example 3 with a standard krasnogorite $WO_3$ x-ray diffraction.

Ammonium meta tungstate hydrate (5 g), carbohydrazide [fuel] (2 g), ammonium nitrate [oxidizier] (10 g), and platinum tetra-amine di-nitrate (1.826 mg from stock solution) were dissolved in 30 ml of deionized (DI) water. The aqueous solution was then placed in a muffle furnace, which had been preheated to about 420° C., and then heated for about 15 min or until combustion of the materials was substantially completed. After the combustion of the sample material was completed, the product was annealed in air at about 420° C. for an additional about 15 min. The body color of the powder appeared orange-yellow and Pt doped WO$_3$ was confirmed by comparison of powder XRD pattern with a standard krasnogorite WO$_3$ x-ray diffraction (ICFF PDF card number 071-0131) (FIG. 4). Similarly, three more batches of the process were repeated.

Example 4

Making 0.02 wt. % Ratio Pd Doped Gamma Phase WO$_3$

Figure 5:
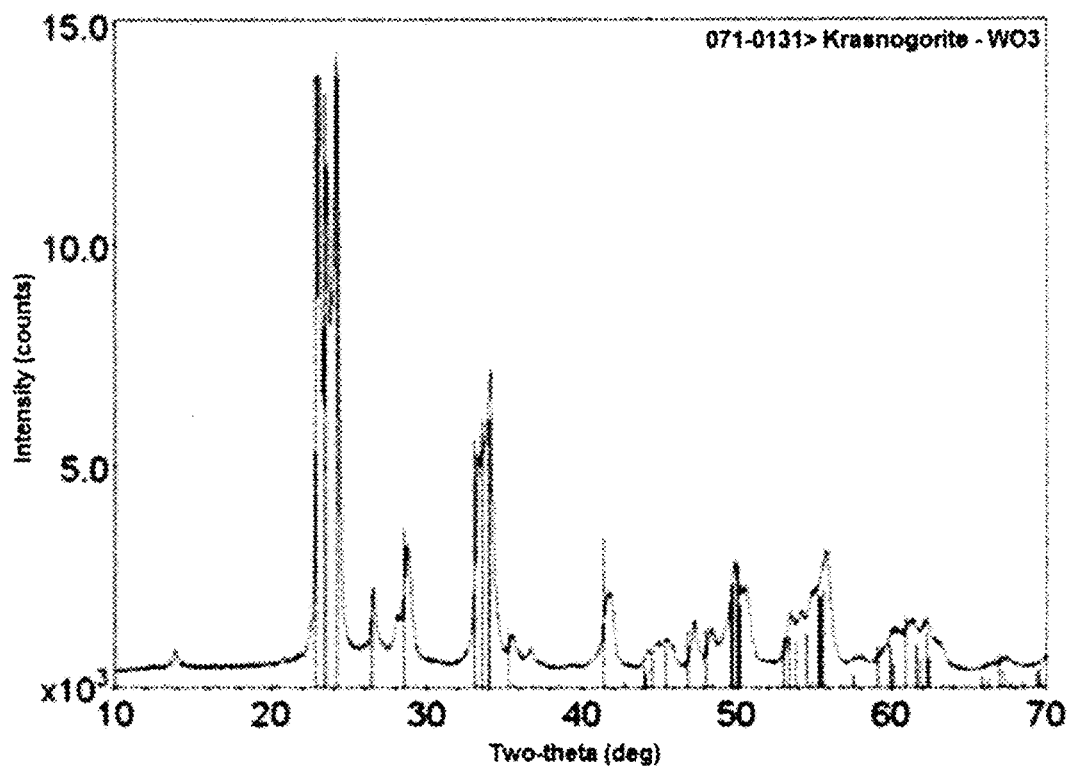
FIG. 5 is a graph showing a result of comparison of powder XRD pattern of Pd doped $WO_3$ prepared in Example 4 with a standard krasnogorite $WO_3$ x-ray diffraction.

Ammonium meta tungstate hydrate (5 g), carbohydrazide [fuel] (2 g), ammonium nitrate [oxidizier] (10 g), and palladium di-nitrate (2.30 mg from stock solution) were dissolved in 30 ml of deionized (DI) water. The aqueous solution was then placed in a muffle furnace, which had been preheated to about 420° C., and then heated for about 15 min or until combustion of the materials was substantially completed. After the combustion of the sample material was completed, the product was annealed in air at about 420° C. for an additional about 15 min. The body color of the powder appeared orange-yellow and Pd doped $WO_3$ was confirmed by comparison of powder XRD pattern with a standard krasnogorite $WO_3$ x-ray diffraction (ICFF PDF card number 071-0131) (FIG. 5). Similarly, three more batches of the process were repeated.

Example 5

Making 0.02 wt. % Ratio Fe Doped Gamma Phase $WO_3$

Figure 6:
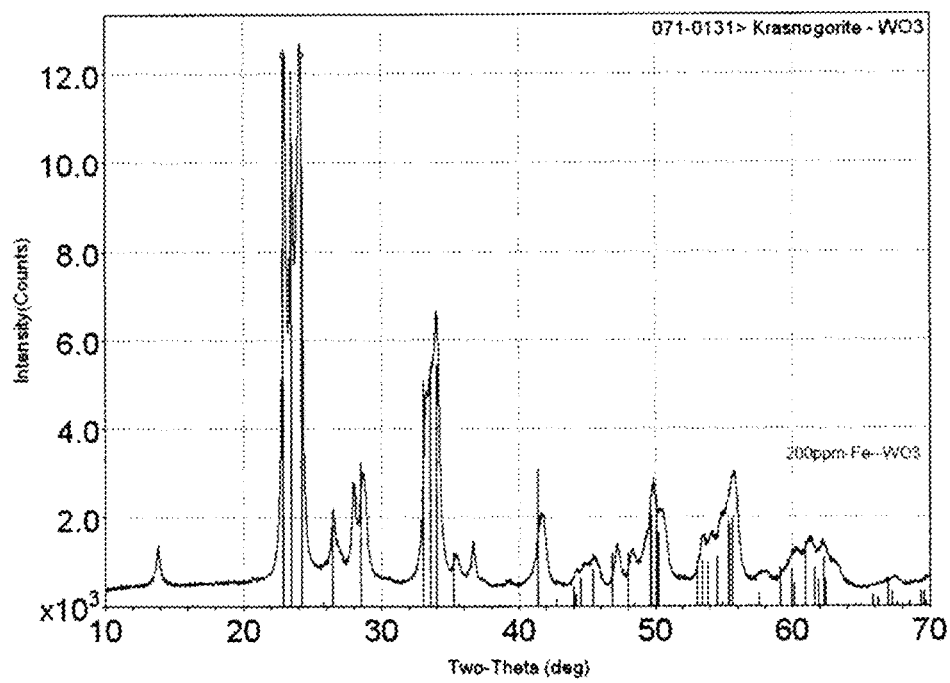
FIG. 6 is a graph showing a result of comparison of powder XRD pattern of Fe doped $WO_3$ prepared in Example 5 with a standard krasnogorite $WO_3$ x-ray diffraction.

Ammonium meta tungstate hydrate (5 g), carbohydrazide [fuel] (2 g), ammonium nitrate [oxidizier] (10 g), and ferric nitrate hexahydrate (6.655 mg from stock solution) were dissolved in 35 ml of deionized (DI) water. The aqueous solution was then placed in a muffle furnace, which had been preheated to about 420° C., and then heated for about 15 min or until combustion of the materials was substantially completed. After the combustion of the sample material was completed, the product was annealed in air at about 420° C. for an additional about 15 min. The body color of the powder appeared orange-yellow and Fe doped $WO_3$ was confirmed by comparison of powder XRD pattern with a standard krasnogorite $WO_3$ x-ray diffraction (ICFF PDF card number 071-0131) (FIG. 6). Similarly, three more batches of the process were repeated.

Example 6

Making $Fe_2O_3$

Figure 7:
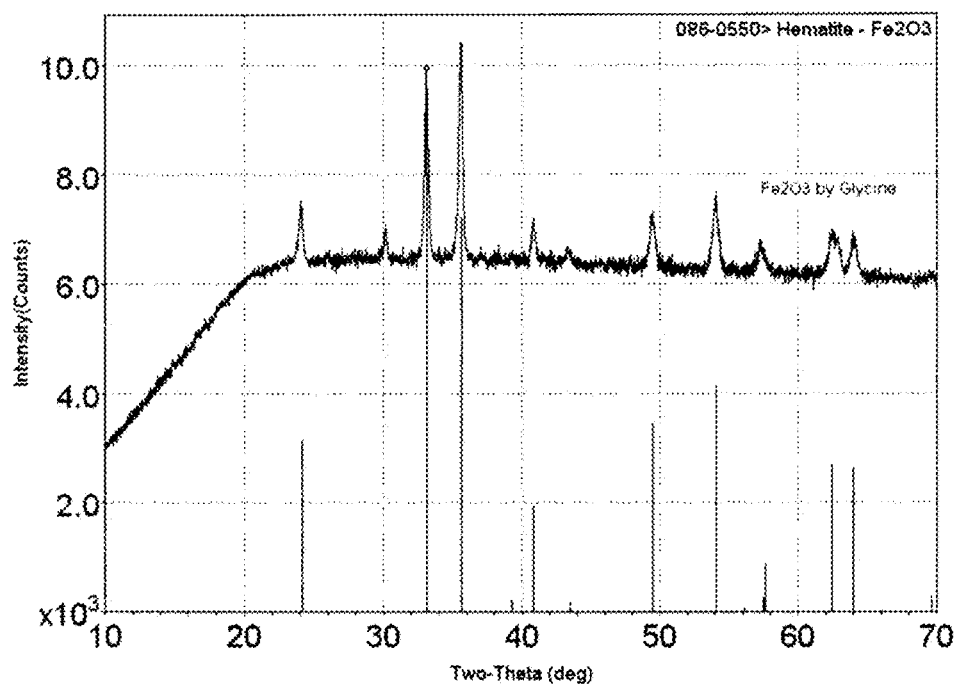
FIG. 7 is a graph showing a result of comparison of powder XRD pattern of $Fe_2O_3$ prepared in Example 6 with a standard hematite $Fe_2O_3$ x-ray diffraction.

Ferric nitrate hexahydrate (10 g) and glycine [fuel] (3.33 g) were dissolved in 20 ml of deionized (DI) water. The aqueous solution was then placed in a muffle furnace, which had been preheated to about 350° C., and then heated for about 20-30 min or until combustion of the materials was substantially completed. After the combustion of the sample material was completed, the product was annealed in air at about 350° C. for an additional about 15 min. The body color of the powder appeared brown and $Fe_2O_3$ was confirmed by comparison of powder XRD pattern with a standard hematite $Fe_2O_3$ x-ray diffraction (ICFF PDF card number 086-0550) (FIG. 7). Similarly, three more batches of the process were repeated.

Example 7

Making Epsilon Phase $(W,B)O_3$ and $CeO_2$ Physical Mixture by Acoustic Mixing 12 g of boron doped epsilon phase $WO_3$ prepared in Example 1 above and 8.9 g of $CeO_2$ were mixed by acoustic mixer with 35% acceleration and 40Gs intensity for about 5 minutes in a plastic container.

Example 8

Making Gamma Phase $WO_3$ and $CeO_2$ Physical Mixture by Acoustic Mixing 12 g of gamma phase $WO_3$ prepared in Example 2 above and 8.9 g of $CeO_2$ were mixed by acoustic mixer with 35% acceleration and 40Gs intensity for about 5 minutes in a plastic container.

Example 9

Making 0.02 wt. % Ratio Pt Doped Gamma Phase $WO_3$ and $CeO_2$ Physical Mixture by Acoustic Mixing 12 g of 0.02 wt. % ratio Pt doped gamma phase $WO_3$ prepared in Example 3 above and 8.9g of $CeO_2$ were mixed by acoustic mixer with 35% acceleration and 40Gs intensity for about 5 minutes in a plastic container.

Example 10

Making 0.02 wt. % Ratio Pt Doped Epsilon Phase $(W,B)O_3$ and $CeO_2$ Physical Mixture by Acoustic Mixing 12 g of 0.02 wt. % ratio Pt doped epsilon phase $(W,B)O_3$ and 8.9 g of $CeO_2$ were mixed by acoustic mixer with 35% acceleration and 40Gs intensity for about 5 minutes in a plastic container.
(The Producing Method of Pt Doped Epsilon Phase(W,B)$O_3$)
5 g of ammonium metatungstate (AMT) hydrate (Aldrich), 100 mg of boric acid (Aldrich), 1.826 mg of $Pt(NH_3)_4 \cdot (NO_3)_2$ (Aldrich), 2 g of carbohydrazide (Aldrich) and 10 g of ammonium nitrate (Aldrich) were dissolved in 50 ml of deionized (DI) water. The aqueous solution was then placed in a muffle furnace, which had been preheated to about 420° C., and then heated for about 20 min or until combustion of the materials was substantially completed. After the combustion of the sample material was completed, the product was annealed in air at about 420° C. for an additional about 20 min. The resultant powder was confirmed to be Pt-doped and boron-doped $WO_3$ by comparison of the measured XRD pattern with a standard ε-$WO_3$ x-ray diffraction (ICFF PDF card number 01-087-2404).

Example 11

Making 0.02 wt. % Ratio Fe Doped Gamma Phase $WO_3$ and $CeO_2$ Physical Mixture by Acoustic Mixing 12 g of 0.02 wt. % ratio Fe doped gamma phase $WO_3$ prepared in Example 5 above and 8.9g $CeO_2$ were mixed by acoustic mixer with 35% acceleration and 40Gs intensity for about 5 minutes in a plastic container.

Example 12

Photocatalyst Material Coating on Alumina Ceramic Filter 18.75 g of photocatalyst powder (example 8: gamma $WO_3$+$CeO_2$ physical mixture) was thoroughly mixed with 60 g of de-ionized water by thinky mixing (2000 rpm for 2 min) followed by probe sonication method (15 Hz for 30 minutes). This uniform slurry was transferred into Petri dish (size), and one side of alumina ceramic filter, 100 mm×50 mm×5 mm rectangular size or 50 mm×50 mm×5 mm square (pretreated by annealing at 800° C. for overnight) was soaked in the photocatalyst powder slurry for about 1 min, then flip over to another side for another 1 min. This process was repeated for additional 2 times (thus total of 6 minutes for one filter is called one coating). After the each coating process, excess slurry present in the alumina ceramic filter was removed by spin coating and then, dried at 150° C. for about 1 h. The one coating process if necessary repeated for two or three times coatings were done after drying at 150° C. for about 10 minutes. Finally, the photocatalyst coated alumina ceramic filter was annealed at 400° C. in air in the muffle furnace for about 3 h.

Example 13

Ethylene Removal

Figure 8:
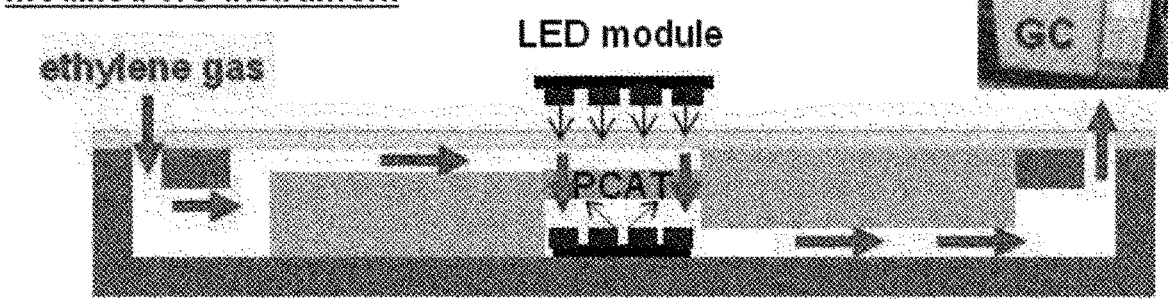
FIG. 8 is a schematic view of the testing chamber used to evaluate the rate of ethylene decomposition by the photocatalytic element in the Examples.
Figure 9:
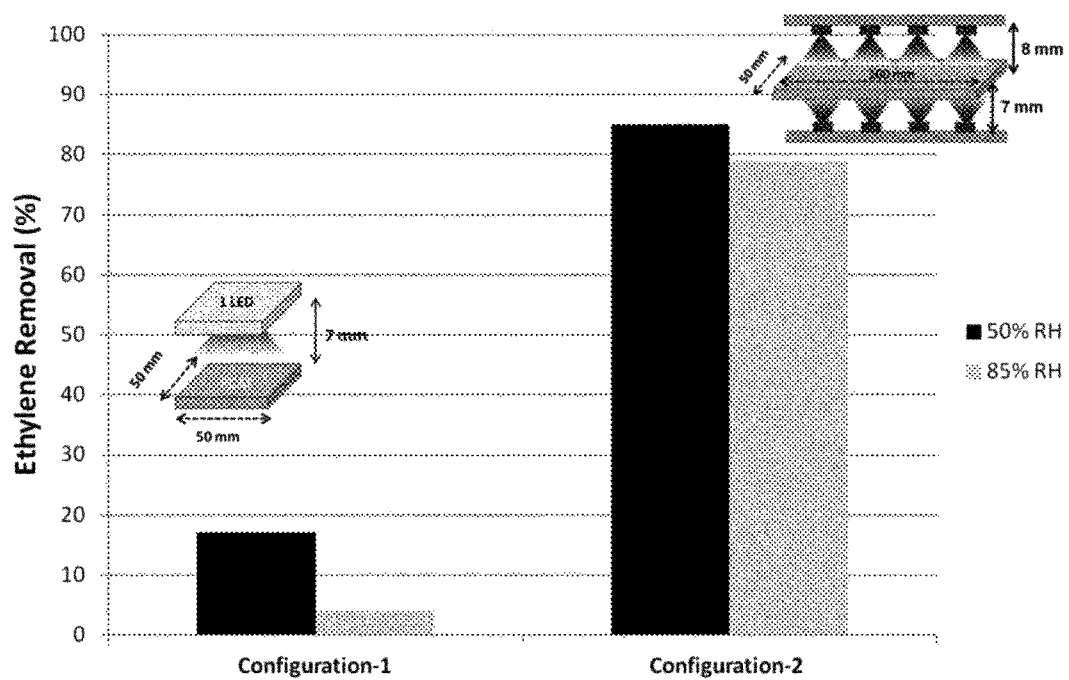
FIG. 9 is a graph of the results of the ethylene decomposition test of Example 13.
Figure 10A:
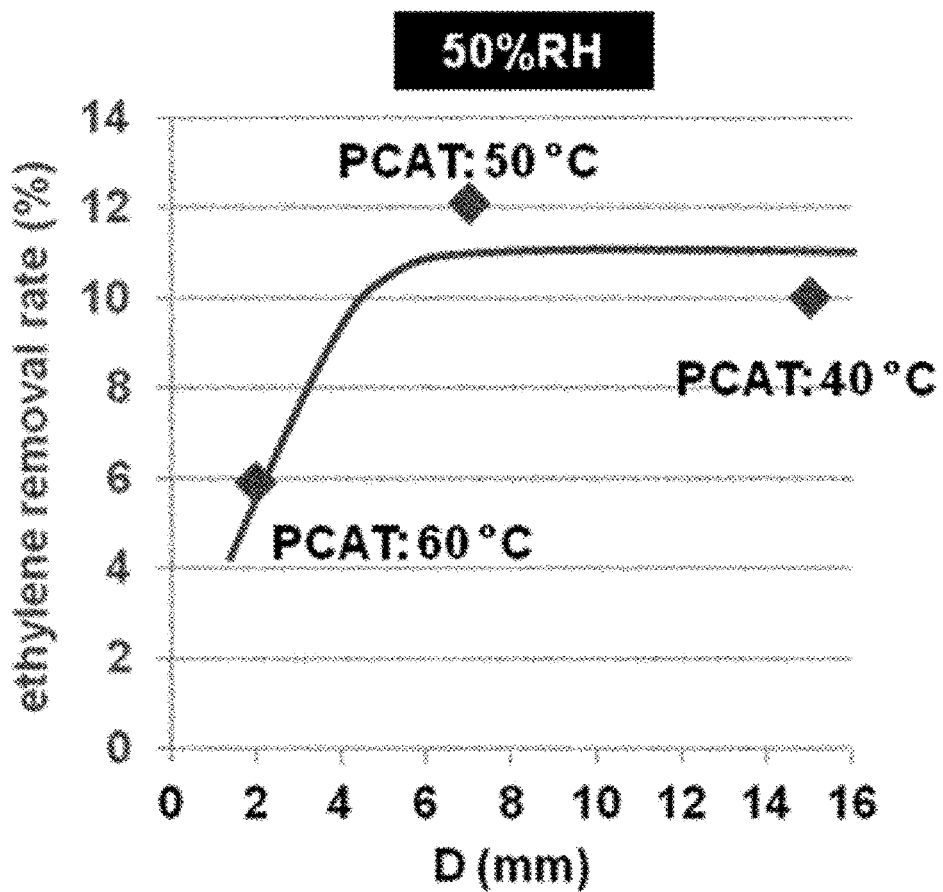
FIG. 10A is a graph of the results of ethylene decomposition test of an embodiment varying D at 50% RH.
Figure 10B:
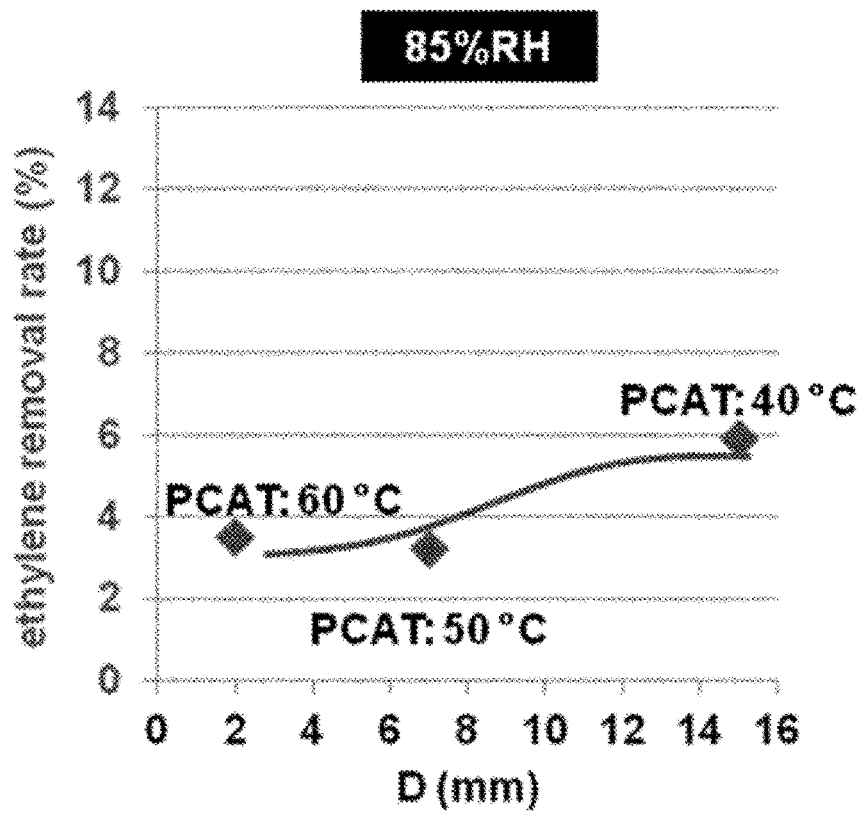
FIG. 10B is a graph of the results of ethylene decomposition test of an embodiment varying D at 85% RH.
Figure 11:
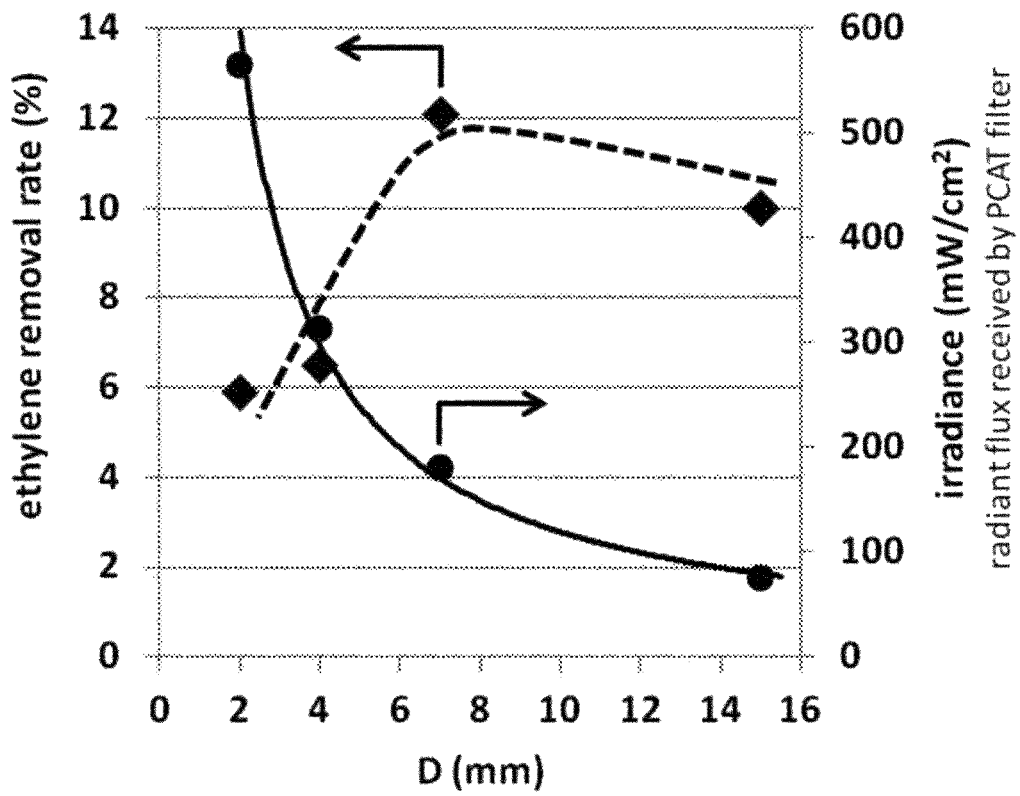
FIG. 11 is a graph of the results of ethylene decomposition test of an embodiment varying irradiance at 50% RH.

The prepared 50 mm×50 mm×5 mm sized photocatalyst coated ceramic filter of Example 12 was placed in a flat reaction chamber, and evaluated in a manner similar to the industrial standard evaluation JIS R1701/ISO22197-1, except as described herein, e.g., that ethylene was tested instead of acetylaldehyde. See FIG. 8. The inlet of the testing chamber supplied a continuous 1 Liter per minute flow of 5 ppm ethylene-containing purified air mixture. The mixture had a relative humidity of about 50%, controlled by a moisturizer/mass flow controller. The light source to activate visible light photocatalyst was a blue LED array (445 nm), with a current set from about 50 mA to about 800 mA at a distance from the LED to the prepared ceramic set from about 2 mm to about 15 mm. The irradiation period was about 12 hours. Irradiance (power intensity) at the surface of the sample filter was measured about 75 mW/cm$^2$ to about 565 mW/cm$^2$. The temperature of the ceramic surface proximal to the LED was measured. The concentration of ethylene in the gas was measured at the outlet by a gas chromatoagraphy-flame ionization detector (GC-FID). The difference in ethylene concentration between the inlet and outlet shows the photocatalyst activity. The distance from the LED to the photocatalytic element surface was varied between 2, 4, 7, and/or 15 mm, the RH of the sample fluid flow was varied between 50% relative humidity and 85% relative humidity, and the current flow to the LED were varied. To maximize light irradiation to a single PCAT filter (50 mm×50 mm×5 mm) we used a reflector or another LED on the opposite of the filter. The results are depicted in Tables 1-2 and FIGS. 10A-11. Then a larger dimension of PCAT filter (100 mm×50 mm×5 mm) was used with multiple irradiation sources from top and bottom (4-LED from top and 4-LED from bottom) at a distance about 7 and 8 mm from PCAT surface respectively. The optimum ethylene removal efficiency was measured by GC-FID. The optimum results of ethylene removal efficiency by using single irradiation (configuration-1) and multiple irradiation (configuration-2) are shown in FIG. 9. Photothermal effect became dominant with configuration-2, where any water molecules readily removed from the PCAT surface and hence showed higher ethylene removal efficiency at high relative humidity.

Figure 12:
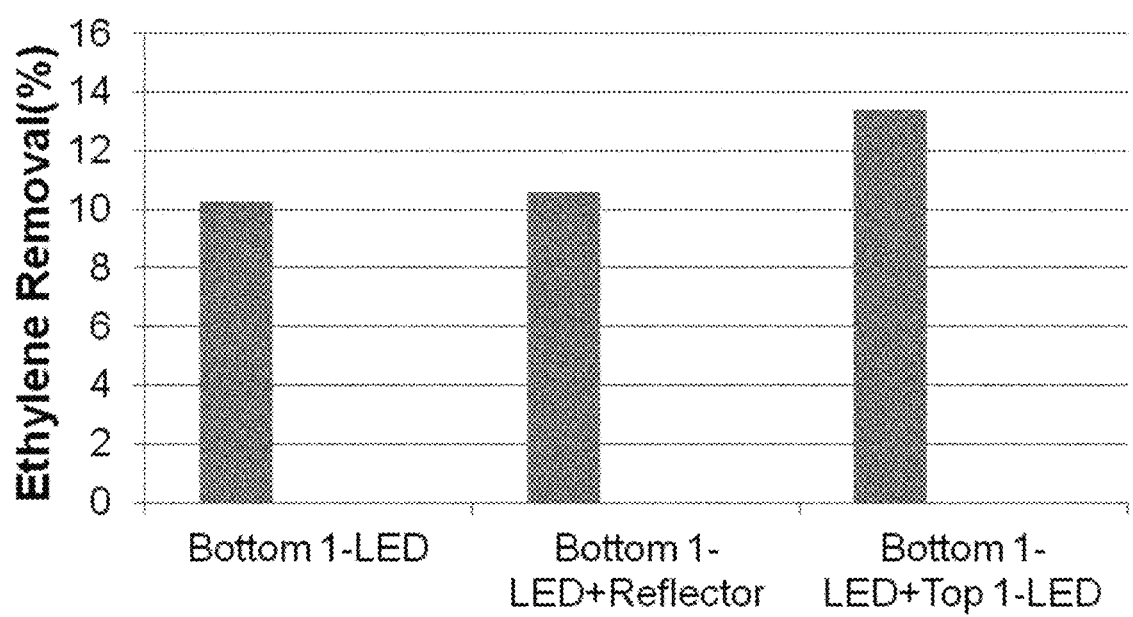
FIG. 12 is a graph of the results of ethylene decomposition test of an embodiment with a single light emitting source; a single light emitting source and a reflector element; and a dual light emitting source embodiment at 50% RH.

In another example, a second LED was placed a distance of about 8 mm from the second surface of the photocatalytic material in the JIS reaction chamber described above. In other similar examples, a reflector e.g. 100 nm silver coated glass was placed 8 mm from the photocatalytic material instead of the second LED. The surface temperature was measured at about 50° C. The results of these later embodiments are shown in FIG. 12.

TABLE 1

| d (mm) | 15 | 7 | 4 | 2 |
|---|---|---|---|---|
| Irradiance (mW/cm$^2$) | 75 | 181 | 313 | 565 |

TABLE 2

| d (mm) | 15 | 7 | 4 | 2 |
|---|---|---|---|---|
| Temperature (° C.) | 40 | 50 | 56 | 60 |

Embodiments

The following embodiments are contemplated as a non-limiting list of applications of the subject matter of the present disclosure.

Embodiment 1

A photocatalytic element comprising:
a photocatalytic layer comprising at least one photocatalytic material; and
a light emitting source in optical communication with the photocatalytic material, the light emitting source disposed sufficiently proximal to the photocatalytic material to raise the surface temperature of at least some of the photocatalytic material to a temperature between 10° C. and 90° C.

Embodiment 2

The photocatalytic element of embodiment 1, wherein the light emitting source is sufficiently proximal to the photocatalytic element to provide at least 50% reduction in volatile organic compounds in an environment of above 45% relative humidity.

Embodiment 3

The photocatalytic element of embodiment 1 or 2, wherein the light emitting source is sufficiently proximal to substantially cover at least 75% of the photocatalytic surface area.

Embodiment 4

The photocatalytic element of any one of embodiments 1 to 3, wherein the light emitting source is sufficiently proximal to raise the surface temperature of the photocatalytic material to at least 40° C.

Embodiment 5

The photocatalytic element of any one of embodiments 1 to 4, wherein the light emitting source is a light emitting diode (LED).

Embodiment 6

The photocatalytic element of any one of embodiments 1 to 5, wherein the photocatalytic material is an oxide semiconductor having the energy level of the valence band to be lower than 2.85 eV.

Embodiment 7

The photocatalytic element of any one of embodiments 1 to 6, wherein the photocatalytic material has an optical band gap of at least 2.6 eV.

Embodiment 8

The photocatalytic element of any one of embodiments 1 to 7, wherein the photocatalytic material is $WO_3$.

Embodiment 9

The photocatalytic element of any one of embodiments 1 to 8, wherein the photocatalytic layer further comprises at least one co-catalyst.

Embodiment 10

The photocatalytic element of embodiment 9, wherein the co-catalyst is selected from at least one semiconducting metal oxides or sulphides.

Embodiment 11

The photocatalytic element of embodiment 9 or 10, wherein the valence band energy level of the co-catalyst is higher than that of the photocatalytic material.

Embodiment 12

The photocatalytic element of any one of embodiments 9 to 11, wherein the co-catalyst is selected from $(Ce, Sn)O_2$, $TiO_2$, alkaline titanate, alkali tantalate, and alkali niobate.

Embodiment 13

The photocatalytic element of any one of embodiments 1 to 12, wherein the photocatalytic layer further comprises at least one catalyst promoter.

Embodiment 14

The photocatalytic element of embodiment 13, wherein the catalyst promoter is doped and/or loaded with at least one metal selected from Cu, Fe, Au, Ag, Pt, Pd, Ir, Ru, and Rh or their oxides and hydroxides.

Embodiment 15

The photocatalytic element of embodiment 13 or 14, wherein the concentration of the catalyst promoter is at least 10 ppm.

Embodiment 16

The photocatalytic element of any one of embodiments 13 to 15, wherein the at least one catalyst promoter has at least two electron oxygen reduction functionality.

Embodiment 17

The photocatalytic element of any one of embodiments 1 to 16 wherein the light emitting source delivers at least 10 $mW/cm^2$ energy at the photocatalytic surface.

Embodiment 18

The photocatalytic element of any of embodiments 1 to 17, wherein the light emitting source provides light irradiation upon at least 5% surface area of the photocatalytic layer.

Embodiment 19

The photocatalytic element of any one of embodiments 1 to 18, wherein the light emitting source provides light irradiation at least at one side of the photocatalytic layer.

Embodiment 20

The photocatalytic element of any one of embodiments 1 to 19, wherein the optical configuration provides light irradiation at multiple sides of the photocatalytic layer.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

The terms "a," "an," "the" and similar referents used in the context of describing the invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of any claim. No language in the specification should be construed as indicating any non-claimed element essential to the practice of the invention.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, the claims include all modifications and equivalents of the subject matter recited in the claims as permitted by applicable law. Moreover, any combination of the above-described elements in all possible variations thereof is contemplated unless otherwise indicated herein or otherwise clearly contradicted by context.

In closing, it is to be understood that the embodiments disclosed herein are illustrative of the principles of the claims. Other modifications that may be employed are within the scope of the claims. Thus, by way of example, but not of limitation, alternative embodiments may be utilized in accordance with the teachings herein. Accordingly, the claims are not limited to embodiments precisely as shown and described.

The invention claimed is:

1. A photocatalytic element comprising: a photocatalytic layer comprising at least one photocatalytic material, wherein the photocatalytic material has an optical band gap of at least 2.6 eV; and
   a light emitting source in an optical communication configuration with the photocatalytic material, the light emitting source disposed within 15 mm of the photocatalytic material, wherein a surface temperature of at least some of the at least one photocatalytic material is raised to a temperature between 40° C. and 90° C. by irradiating said photocatalytic material with said light emitting source, and wherein the optical communication configuration that provides light irradiation at multiple sides of the photocatalytic layer comprises a first light emitting source configured or disposed on a first side of the photocatalytic element, and a second light emitting source configured or disposed on a second side of the photocatalytic element.

2. The photocatalytic element according to claim 1, wherein the light emitting source is sufficiently proximal to the photocatalytic element to provide at least 50% reduction in volatile organic compounds in an environment of above 45% relative humidity.

3. The photocatalytic element according to claim 1, wherein the light emitting source is sufficiently proximal to substantially cover at least 75% of the photocatalytic surface area.

4. The photocatalytic element according to claim 1, wherein the light emitting source is a light emitting diode (LED).

5. The photocatalytic element according to claim 1, wherein the photocatalytic material is an oxide semiconductor having the energy level of the valence band lower than 2.85 eV.

6. The photocatalytic element according to claim 1, wherein the photocatalytic material is $WO_3$.

7. The photocatalytic element according to claim 1, wherein the photocatalytic layer further comprises at least one co-catalyst.

8. The photocatalytic element according to claim 7, wherein the co-catalyst is selected from at least one semiconducting metal oxide or sulphide.

9. The photocatalytic element according to claim 7, wherein the valence band energy level of the co-catalyst is higher than that of the photocatalytic material.

10. The photocatalytic element according to claim 1, wherein the photocatalytic layer comprises at least one co-catalyst, wherein the co-catalyst is selected from $(Ce,Sn)O_2$, $TiO_2$, alkaline titanate, alkali tantalate, and alkali niobate.

11. The photocatalytic element according to claim 1, wherein the photocatalytic layer further comprises at least one catalyst promoter.

12. The photocatalytic element according to claim 11, wherein the catalyst promoter is doped and/or loaded with at least one metal selected from Cu, Fe, Au, Ag, Pt, Pd, Ir, Ru, and Rh or their oxides and hydroxides.

13. The photocatalytic element according to claim 11, wherein the concentration of the catalyst promoter is at least 10 ppm.

14. The photocatalytic element according to claim 11, wherein the at least one catalyst promoter has at least two electron oxygen reduction functionality.

15. The photocatalytic element according to claim 1, wherein the light emitting source delivers at least 10 $mW/cm^2$ energy at the photocatalytic surface.

16. The photocatalytic element according to claim 1, wherein the light emitting source provides light irradiation upon at least 5% surface area of the photocatalytic layer.

* * * * *